Figure 1:
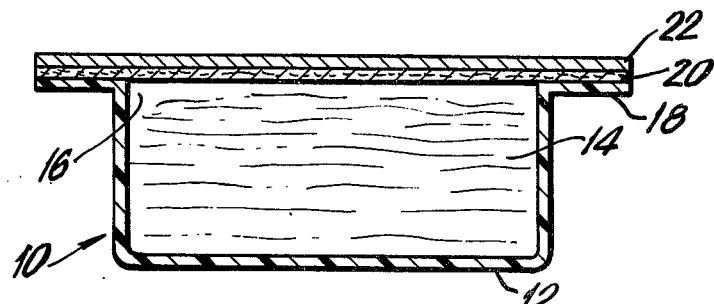

United States Patent [19]

Schwartz

[11] 4,157,787
[45] Jun. 12, 1979

[54] AIR FRESHENER DISPENSER

[75] Inventor: Burton Schwartz, Morris Plains, N.J.

[73] Assignee: Milpak Incorporated, Plainfield, N.J.

[21] Appl. No.: 827,022

[22] Filed: Aug. 23, 1977

[51] Int. Cl.² ............................................... A61L 9/04
[52] U.S. Cl. ..................................... 239/56; 239/60
[58] Field of Search ................... 239/53–56, 239/57, 60

[56] References Cited

U.S. PATENT DOCUMENTS

| 1,898,621 | 2/1933 | Ferguson | 239/57 |
| 2,564,860 | 8/1951 | Ryberg | 239/54 |
| 2,615,754 | 10/1952 | Lindenberg | 239/56 X |
| 3,858,807 | 1/1975 | Rabussier et al. | 239/56 |

FOREIGN PATENT DOCUMENTS 1436075  5/1976  United Kingdom ..................... 239/54

*Primary Examiner*—John J. Love
*Assistant Examiner*—Andres Kashnikow
*Attorney, Agent, or Firm*—Hopgood, Calimafde, Kalil, Blaustein & Lieberman

[57] ABSTRACT

A package and dispenser for a volatile air-treating or air-freshener material includes a container open at its upper end. A first layer of a porous material is permanently secured to the open end of the container and a second layer of a non-porous material is removably secured to the container over the porous layer. When it is desired to use the container to release vaporized air-freshener material, the second layer is removed and the remaining porous layer allows the air-freshening vapor to permeate therethrough while at the same time retaining the remaining non-volatized material within the container.

5 Claims, 2 Drawing Figures

AIR FRESHENER DISPENSER

The present invention relates generally to a dispenser for an air-treating or air-freshener agent, and more particularly to a dispenser which has a removable sealing layer to prevent the air-treating material from being released into the surrounding atmosphere when the dispenser is not in use.

The use of air-treating or air-freshener agents has increased substantially in recent years. Air fresheners are now widely used, for example, in the home, in the office, and in automobiles and boats to provide a more pleasant odor and to remove unpleasant odors in the surrounding atmosphere. As shown in U.S. Pat. No. 3,797,742, a conventional air-freshener dispenser is in the form of a packet which contains a quantity of air-treating material, which may typically be in the form of a powder, a large granule, or a solid pad or a pad saturated with a liquid, which, when exposed to the surrounding atmosphere, gives off a vapor at a controlled rate.

When the air-freshener material is exposed to the atmosphere, it slowly vaporizes and the evaporated material is dispersed in vapor form. That is, once it is exposed to the atmosphere, the air-freshening material begins to vaporize and will eventually be consumed in the event of continued exposure to the atmosphere. To prevent the air-freshener material from becoming either partially or totally depleted or used up by evaporation during its period of storage or shipment, the conventional air-freshener dispenser is typically sealed with a cover layer made of a nonporous material such as paper, plastic, or metal. When the dispenser is not in use, such as during storage or shipment, this layer prevents the air-treating material in the dispenser from vaporizing and becoming prematurely used up. When it is desired to utilize the dispenser to cause some of the air-freshener material to be evaporated into the air, and thereby improve the quality and odor of the surrounding air, the nonporous cover layer is removed, thereby to allow the air-freshener material to evaporate into the surrounding atmosphere.

One disadvantage of the conventional air-freshener dispenser is that once the nonporous cover layer is removed from the conventional air-freshener dispenser, the air-freshener material within the container can be spilled out of the dispenser in the event the dispenser is accidentally knocked over. Should this occur, the air-refresher material may come into contact with furniture, clothing, carpeting and the like, which would produce undesired staining or damage to these articles. Moreover, once the protective cover is removed from the conventional air-freshener dispenser to allow the air-freshener material to evaporate into the atmosphere, the air-freshener material remaining in the dispenser is readily accessible and can thus be touched by a child, who may thereafter put his fingers, which have touched this material, into his mouth or eyes.

It is, therefore, an object of this invention to provide an air-freshener dispenser which prevents the air-freshener material within the container from being spilled or touched when the protective layer is removed from the dispenser to allow the material to volatilize into the surrounding atmosphere.

It is a further and general object of this invention to provide an air-freshener dispenser of the type described which provides the advantages of prior art dispensers while eliminating the disadvantages that are inherent in the prior art air-freshener dispensers.

In accordance with the invention, an air-freshener dispenser includes a container for storing an air-treating or air-freshener material. The container is open at its upper end, which is covered with a first layer made of a porous material. A second, removable and impervious or nonporous layer overlies the first porous layer when the dispenser is not in use, such as when the dispenser is being stored or in shipment. When it is desired to use the dispenser, the upper nonporous layer is removed, and the evaporating material then permeates through the remaining porous layer, which provides the additional function of physically retaining the air-treating material within the container and preventing the material from being touched or inadvertently falling out of the container.

Figure 2:
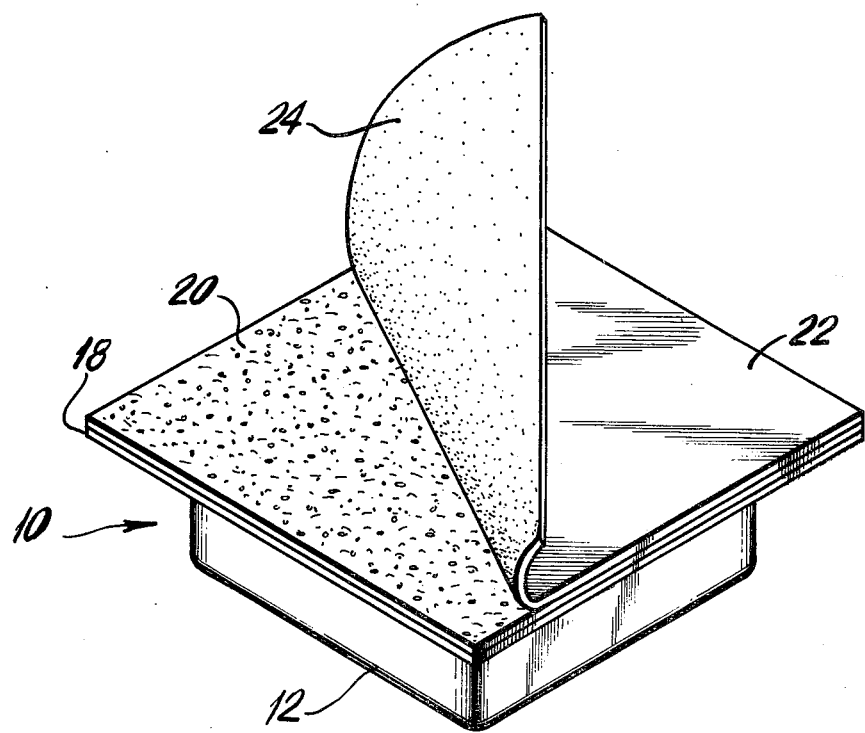

The above and other objects, features and advantages of this invention will be apparent from the following detailed description of an illustrative embodiment thereof which is to be read in conjunction with the accompanying drawing wherein:

FIG. 1 is a cross-sectional view of an improved air-freshener dispenser in accordance with an embodiment of the invention; and FIG. 2 is a perspective view of the improved air-freshener dispenser of FIG. 1, showing the manner in which the upper, non-porous layer is removed from the dispenser when the dispenser is to be used.

Referring to FIG. 1, there is shown an improved air-freshener dispenser, which is generally designated 10, and which includes a chamber or a container 12 for storing a quantity of an air-treating or air-freshener material 14. Material 14, which may be in the form of a powder, a liquid, a solid, or a pad saturated with a liquid material, has the characteristic that it volatilizes into the surrounding atmosphere when it is exposed to the air.

Container 12 has an opening 16 at its upper end, which is surrounded by a peripheral flange 18. The open upper end of the container 12 is covered with a porous layer 20, which is secured to the upper surface of flange 18 such as by an adhesive or sealant coating on the underside of layer 20. According to the invention, layer 20 is porous to the vaporized air-refreshener material which can permeate therethrough. Layer 20 may be made of a material which is itself inherently porous or permeable to the vaporized air-freshener material. Alternatively, layer 20 may be made of a normally nonporous material in which a multiplicity of fine openings are formed, or it may be a porous material with a multiplicity of openings formed thereon to increase the porosity of the layer to the volatilizing material.

An upper removable layer 22, made of material which is nonporous or nonpermeable to the vaporized air-freshener material 14, is removably secured to the upper surface of layer 20 by means such as a peelable adhesive coating 24 on its underside. Alternatively, layer 22 may be removably attached to the upper surface of porous layer 20 by the inclusion of a peelable adhesive or sealant coating on the upper surface of layer 20. Both layers 20 and 22 are placed over the open end of container 12, as shown in FIG. 1, when the dispenser 10 is not in use so as to prevent the air-freshener material 14 in the container from evaporating and becoming depleted.

When it is desired to utilize the air-freshener dispenser to allow the air-freshener material to permeate into the surrounding atmosphere, the upper removable layer 22 is peeled away or otherwise removed from the dispenser, as shown in FIG. 2. The underlying porous layer 20 remains in place over the open end of container 12. Layer 20, since it is formed of a foraminous or otherwise porous material, allows the volatized air-freshener material to permeate therethrough into the surrounding atmosphere. At the same time, layer 20 retains the non-volatized air-refreshener material 14 within the container, thereby preventing the material from spilling or falling out of the container if the dispenser should be inadvertently tipped over or spilled, and also prevents a child from touching the material within the container.

Container 12, which contains the volatile air-freshener material, is thus covered at all times with a layer of porous material through which vaporized air-freshener material can permeate, and which also physically retains the air-freshener material within the chamber. When the dispenser is not in use, the container is further sealed with a second layer of nonporous material which prevents the air-freshener material from permeating into the surrounding atmosphere and thus prevents waste of the air-freshener material in the dispenser until it is desired to use the dispenser to allow the air-freshener material to be dispersed into the atmosphere.

It will be appreciated that the container 12, although it is illustrated in the embodiment herein specifically described, as being generally square, can be formed in any desired shape, for example, round or oval, as long as the container is covered with the porous and removable nonporous layers to provide the advantages of the invention as described above. The material of which porous layer 20 may be made includes gauze, tea paper, or vinyl and/or a solid perforated material, such as aluminum foil or the like or a combination of such materials, perforated with a multiplicity of small openings to render the material permeable to the evaporating air-freshener material.

Moreover, although the dispenser of the invention has been described with respect to dispensing an air-freshener material, in the form of a vapor, it may be used to advantage in other applications in which it is desired to have a material diffuse or otherwise permeate out of the dispenser while ensuring that the base material is retained securely in the dispenser.

It will thus also be appreciated that although the air-freshener dispenser of the invention has been herein described with respect to a single embodiment, variations may be made therein without necessarily departing from the spirit and scope of the invention.

What is claimed is:

1. A dispenser comprising a container for containing therein a material which vaporizes upon exposure to the ambient atmosphere, said container having an opening at its upper end and a peripheral flange surrounding said opening, a first layer of a material having a multiplicity of fine aperatures therein secured to said peripheral flange and covering said opening, and a second nonporous layer, being the same size as said first layer and being releasably secured to an upper surface of said first layer for sealing said aperatures in said first layer, whereby said first layer retains the material within said container and said second layer seals said container to permit storage of said material.

2. A dispenser comprising a container for containing therein a material which vaporizes upon exposure to the ambient atmosphere, said container having an opening at its upper end and a peripheral flange surrounding said opening, a first layer of a material that is porous to the vaporized material secured to said periperhal flange and covering the upper end of said container, and a second nonporous layer releasably secured to and overlying said first layer and effective when in place over said first layer to prevent evaporating material from passing therethrough into the surrounding atmosphere, said first layer being effective when said second layer is at least partially removed therefrom to retain the material in said container while allowing the vaporized material to permeate therethrough into the surrounding atmosphere.

3. The dispenser of claim 2, in which said first layer is fixedly secured to the upper perimeter of said container.

4. The dispenser of claim 2, in which said first layer comprises a sheet of material having a multiplicity of fine openings formed therein.

5. The dispenser of claim 3, in which said second layer is releasably attached to the upper surface of said first layer.

* * * * *